United States Patent
Javet et al.

(10) Patent No.: US 7,214,248 B1
(45) Date of Patent: *May 8, 2007

(54) MULTI-COMPONENT KIT AND METHOD FOR TEMPORARILY DYEING AND LATER DECOLORIZING HAIR

(75) Inventors: Manuela Javet, Marly (CH); Catherine Mueller, Marly (CH); Sylviane Oberson, Farvagny (CH); Gisela Umbricht, Marly (CH); Hans-Juergen Braun, Ueberstorf (CH); Otto Goettel, Marly (CH); Andre Hayoz, Senedes (CH)

(73) Assignee: Wella AG, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/601,431

(22) PCT Filed: Nov. 23, 1999

(86) PCT No.: PCT/EP99/09005

§ 371 (c)(1),
(2), (4) Date: Aug. 2, 2000

(87) PCT Pub. No.: WO00/33799

PCT Pub. Date: Jun. 15, 2000

(30) Foreign Application Priority Data

| Dec. 7, 1998 | (DE) | 198 56 342 |
| May 12, 1999 | (DE) | 299 08 464 U |
| Jul. 16, 1999 | (DE) | 199 33 313 |
| Jul. 21, 1999 | (DE) | 199 34 283 |

(51) Int. Cl.
*A61K 7/13* (2006.01)
*A61K 7/135* (2006.01)

(52) U.S. Cl. .................... 8/405; 8/102; 8/110; 8/429
(58) Field of Classification Search ............... 8/405, 8/429, 102, 110
See application file for complete search history.

(56) References Cited

U.S. PATENT DOCUMENTS

| 3,800,809 | A |   | 4/1974 | Saad |
| 4,513,142 | A | * | 4/1985 | Raue et al. ............ 548/507 |
| 4,542,223 | A | * | 9/1985 | Raue et al. ............ 548/455 |
| 4,542,224 | A | * | 9/1985 | Raue et al. ............ 548/455 |
| 6,171,347 | B1 | * | 1/2001 | Kunz et al. ............ 8/407 |
| 6,179,883 | B1 | * | 1/2001 | Terranova et al. ........ 8/423 |
| 6,371,993 | B1 |   | 4/2002 | Moeller et al. |
| 6,652,601 | B2 | * | 11/2003 | Sauter et al. ........... 8/405 |
| 6,669,739 | B2 | * | 12/2003 | Sauter et al. ........... 8/405 |
| 6,740,128 | B2 | * | 5/2004 | Javet et al. ............ 8/405 |
| 7,056,348 | B2 | * | 6/2006 | Sauter et al. ........... 8/405 |

FOREIGN PATENT DOCUMENTS

| DE | 197 17 222 A1 | 10/1998 |
| DE | 197 17 223 A1 | 10/1998 |
| DE | 197 17 224 A1 | 10/1998 |
| DE | 197 17 280 A1 | 10/1998 |
| DE | 197 16 780 C1 | 11/1998 |
| DE | 197 32 016 A1 | 1/1999 |
| DE | 197 45 292 A1 | 4/1999 |
| EP | 0 370 492 A | 5/1990 |
| EP | 0 376 776 A | 7/1990 |
| EP | 0 497 697 A | 8/1992 |
| EP | 0 826 668 A | 3/1998 |
| WO | WO 98/22078 | * 5/1998 |

OTHER PUBLICATIONS

W. Umbach "Kosmetik, Enywicklung, Herstellung U . . . " Georg Thieme Verlag, Stuttgart, P. 284, 1998.
K. H. Schrader: "Grundlagen Und Rezepturen Der Kosmetika", 2. Auflage (1989), pp. 807-808.

* cited by examiner

*Primary Examiner*—Lorna M. Douyon
*Assistant Examiner*—Amina Khan
(74) *Attorney, Agent, or Firm*—Michael J. Striker

(57) ABSTRACT

The composition for dyeing fibers is obtained before use by mixing a first component A1, containing at least one enamine of the formula (I)

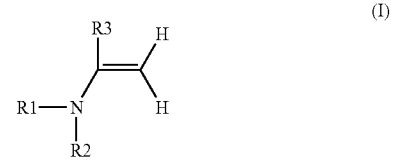

with a second component A2, containing at least one carbonyl compound. A multi-component kit for dyeing and, later on, decolorizing fibers, and a method for temporarily dyeing hair with the composition for dyeing fibers and later removing the dyed hair color with a decolorizing component B containing a sulfite are also provided. The multi-component kit for dyeing and, later on, decolorizing fibers, separately contains the first component A1, the second component A2 and the decolorizing component B.

14 Claims, No Drawings

MULTI-COMPONENT KIT AND METHOD FOR TEMPORARILY DYEING AND LATER DECOLORIZING HAIR

BACKGROUND OF THE INVENTION

The object of the present invention is a composition, containing aromatic enamines and carbonyl compounds, for dyeing fibers, particularly keratin fibers (such as human hair), a method for dyeing fibers, especially keratin fibers, a multi-component kit for dyeing and, later on, decolorizing fibers, particularly human hair, which kit contains a composition for producing a dyeing of the fibers as well as a composition for the reductive removal of the dyeing, as well as a method for dyeing and later on decolorizing fibers, particularly keratin fibers.

Hair dyeing compositions are divided mainly into the area of oxidation dyes and that of tinting, depending on the initial color of the hair that is to be dyed and on the end result desired. Oxidizing hair dyes are outstandingly suitable for covering larger portions of gray. Oxidizing dyeing agents, which are used when the gray portion does not exceed 50%, generally are referred to as oxidative tints, whereas the oxidizing dyeing agent, used when the gray portion exceeds 50% or for "brighter dyeing", usually are referred to as oxidative dyes. Direct dyes are contained mainly in non-oxidizing dyes (so-called tinting agents). Direct dyes are contained mainly in non-oxidative dyeing agents (so-called tinting agents). Because of their small size, some direct dyes, such as the nitro dyes, can penetrate into the hair and dye it directly, at least in the outer regions. Such tints treat the hair very gently and usually withstand 6 to 8 washings and enable gray to be covered to about 20% to be covered.

In general, direct and oxidative tints are washed out of the hair after a few washings. The time period depends very much on such factors as the structure of the hair and on the shade used. Oxidative dyes can partly fade with time, but usually remain in the hair until it is cut the next time. However, removal of the hair dyeing at any time may be desirable if a particular color is to be worn only for a certain time or if the user is not satisfied with the dyeing. Likewise, when hair dyeing is used for the first time, the possibility of removing the dyeing gently and completely reduces the fear of too drastic a color change ("dyeing as a test").

The German Offenlegungsschrift 197 45 292 discloses the use of a combination of malonaldehyde derivatives, such as malonaldehyde bis-dialkyl acetals, and amines or compounds with an acidic CH group for dyeing hair without the use of oxidizing agents. Likewise, it is known from the state of the art, for example, from K. H. Schrader, "Grundlagen und Rezepturen der Kosmetika (Fundamentals and formulations of cosmetics)", 2$^{nd}$ edition (1989), pages 807 and 808, that so-called stripping agents, which contain active reducing or oxidizing agents, can be used for removal of unsuccessful dyeings. However, such stripping agents cause considerably damage to the hair and remove the dye completely only in rare cases.

SUMMARY OF THE INVENTION

It is the task of the present invention to make a dyeing system available which, without the addition of oxidizing agents (such as hydrogen peroxide), lead on the one hand to a gentle, intensive and permanent dyeing of the fibers and, on the other, make possible a gentle and complete removal of this dyeing at any time.

Surprisingly, it has now been found that, by using a dyeing agent, obtained by mixing an enamine of formula (1) with a dyeing agent containing a carbonyl compound, intensive dyeings are achieved in a gentle manner and can be removed completely at any given later time.

The object of the present invention therefore is a composition for dyeing fibers (A), such as wool, silk, cotton or hair and, in particular, human hair, which is obtained by mixing two components and characterized in that the one component (component A1) contains at least one enamine of formula (I) or its physiologically tolerated salt,

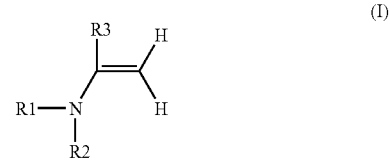

in which R1 is an aromatic group, with one or more aromatic rings, particularly a 5-membered or 6-membered aryl group, preferably a phenyl group, which is optionally substituted by a C1 to C4 alkyl group, a C1 to C4 hydroxyalkyl group, a hydroxy group, a methoxy group, a dialkylamino group or a halogen group or a 5-membered or 6-membered heterocyclic group, preferably a pyridyl group, or a napthyl group; R2 is a linear or branched C1 to C8 alkyl group, a linear or branched C1 to C8 hydroxyalkyl group or a C1 to C8 alkoxyalkyl group, there possibly being oxygen atoms between the carbon atoms of the alkyl chain, R3 is a linear or branched C1 to C8 alkyl group, a C1 to C8 alkoxyalkyl group or a linear or branched C1 to C8 alkylene group, a C1 to C8 alkoxyalkylene group, —O—, —NH—, —NR$_4$— or —S— and R$_4$ is an alkyl group, an alkoxyalkyl group, a hydroxyalkyl group or hydrogen, the R1 and R3 groups, together with the nitrogen atom and the carbon atom of the basic enamine structure being able to form a cyclic compound and the other component (component A2) contains at least one carbonyl compound, particularly an aldehyde.

Preferred are compounds of formula (1), in which the R1 and R3 groups, together with the nitrogen atom and the carbon atom of the basic enamine structure, form a cyclic compound, R3 preferably being connected with the carbon atom of the aromatic R1 group that is in the position ortho to the enamine-substituted carbon atom.

Especially preferred are enamines of formulas (II) to (IX).

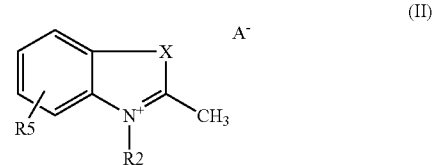

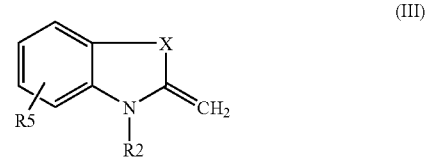

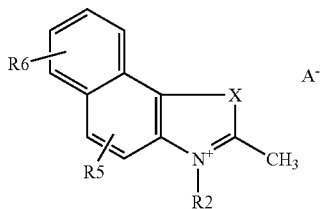
(IV)

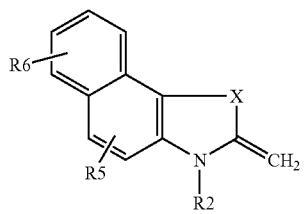
(V)

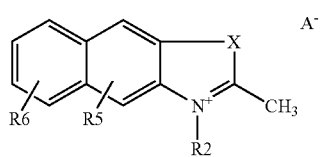
(VI)

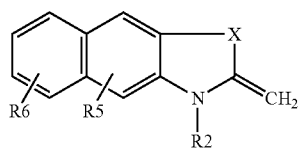
(VII)

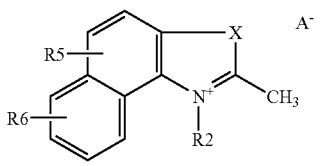
(VIII)

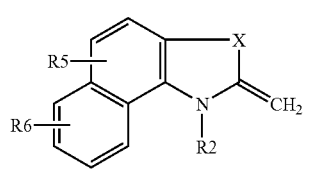
(IX)

in which X is a carbon atom, which is substituted by two C1 to C4 alkyl groups (particularly by two methyl groups) or by a C1 to C4 alkyl group and a hydroxyl group, a sulfur atom, an alkylated or not alkylated nitrogen atom or an oxygen atom, and R2 is a linear or branched C1 to C8 alkyl group, a linear or branched C1 to C8 hydroxyalkyl group or a C1 to C8 alkoxyalkyl group, there possibly being oxygen atoms between the carbon atoms of the alkyl chain, R5 and R6, independently of one another, are hydrogen, a linear or branched C1 to C4 alkyl group, a linear or branched C1 to C4 hydroxyalkyl group, a hydroxy group, a methoxy group, an amino group, a dialkylamino group or a halogen atom, and $A^-$ is chloride, bromide, iodide, hydrogen sulfate, monomethyl sulfate, sulfate, hexafluorophosphate, hexafluoroantimonate, tetrafluoroborate, tetraphenyl borate and preferably chloride, bromide and hydrogen sulfate.

Of the compounds of formulas (I) to (IX), the following are particularly preferred: 3-ethyl-2-methylenebenzothiazolin, 2-methylene-1,3,3-trimethylindolin, 1,2,3,3-tetramethyl-3H-indolinium chloride, 1,2,3,3-tetramethyl-3H-indolinium bromide, 1,2,3,3-tetramethyl-3H-indolinium iodide, 1,2,3,3-tetramethyl-3H-indolinium sulfate, 1,2,3,3-tetramethyl-3H-indolinium hydrogen sulfate, 1,2,3,3-tetramethyl-3H-indolinium methyl sulfate, 1,2,3,3-tetramethyl-3H-indolinium hexafluorophosphates, 1,2,3,3-tetramethyl-3H-indolinium hexafluoroantimonate, 1,2,3,3-tetramethyl-3H-indolinium tetrafluoroborate, 5-chloro-2-methylene-1,3,3-trimethylindolin or its salts, 1-(2-hydroxyethyl)-3,3-dimethyl-2-methylene-indolin or its salts, 1,1,2,3-tetramethyl-1H-benz(e)indolinium chloride, 1,1,2,3-tetramethyl-1H-benz(e)indolinium bromide, 1,1,2,3-tetramethyl-1H-benz(e)indolinium iodide, 1,1,2,3-tetramethyl-1H-benz(e)indolinium sulfate, 1,1,2,3-tetramethyl-1H-benz(e)indolinium hexafluorophosphate, 1,1,2,3-tetramethyl-1H-benz(e)indolinium methyl sulfate, 1,1,2,3-tetramethyl-1H-benz(e)indolinium hexafluoroantimonate and 1,1,2,3-tetramethyl-1H-benz(e)indolinium tetrafluoroborate, The following aldehyde, in particular, are named as suitable carbonyl compounds: vanillin (4-hydroxy-3-methoxybenzaldehyde), isovanillin (3-hydroxy-4-methoxybenzaldehyde), 3,4-dihydroxybenzaldehyde, 4-hydroxybenxaldehyde, 3,5-dimethoxy-4-hydroxybenzaldehyde, 4-dimethylaminobenzaldehyde, 4-methyl-5-imidazolcarboxaldehyde, 4-dimethylaminocinnamaldehyde, 4-hydroxy-2-methoxybenzaldehyde, 3,5-dimethyl-4-hydroxybenzaldehyde, 4-dimethylamino-2-methoxybenzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxybiphenyl-1-carbaldehyde, 2-hydroxy-3-methoxybenzaldehyde, 2,4-dihydroxybenzaldehyde, 3,4-dihydroxybenzaldehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxybenzaldehyde, 2,5-dimethoxybenzaldehyde, 3,5-dimethoxybenzaldehyde, 3,4-dimethoxybenzaldehyde, indole-3-carbaldehyde, benzene-1,4-dicarbaldehyde, 4-ethoxybenzaldehyde, 2-methyl-1,4-naphthoquinone, 4-carboxybenzaldehyde, 4-hydroxy-3-methoxycinnamaldehyde, 3,5-dimethoxy-4-hydroxy-cinnamaldehyde, 3-methoxy-4-(1-pyrrolidinyl)-benzaldehyde, 4-diethylamino-3-methoxybenzaldehyde, 1,2-phthaldehyde, pyrrole-2-aldehyde, thiophene-2-aldehyde, thiophene-3-aldehyde, chromone-3-carboxyaldehyde, 6-methyl-4-oxo-1(4H)-benzopyran-3-carbaldehyde, N-methylpyrrole-2-aldehyde, 5-methylfurfural, 6-hydroxychromene-3-carboxaldehyde, 6-methylindole-3-carboxaldehyde, 4-dibutylaminobenzaldehyde, N-ethylcarbazol-3-aldehyde, 4-diethylamino-2-hydroxybenzaldehyde, 3,4-dimethoxy-5-hydroxybenzaldehyde, 5-(4-(diethylamino)

phenyl-2,4-pentadienal, 2,3-thiophenedicarboxaldehyde, 2,5-thiophenedicarboxaldehyde, 2-methoxy-1-naphthaldehyde, 3-ethoxy-4-hydroxybenzaldehyde, 2-nitrobenzaldehyde, 3-nitrobenzaldehyde and 4-nitrobenzaldehyde.

The enamine and the carbonyl compound are kept separated from one another until shortly before use. As a rule, the inventive dyeing agent consists of a mixture of the two components A1 and A2, namely a dye composition (A1), which contains the enamine and optionally the direct dye, and a further dye composition (A2), which contains the carbonyl compound and optionally direct dyes. These two components are mixed immediately before use into a ready-for-use dyeing agent and then applied on the fibers, which are to be dyed. Of course, it is also possible that one or more of the two components consists of several individual components, which are mixed with one another before use.

The enamines of formula (I) and the carbonyl compounds are contained in the respective dye composition (component A1 or component A2) in each case in a total amount of about 0.02 to 20 percent by weight and preferably of 0.2 to 10 percent by weight, the enamine of formula (I) and the carbonyl compound in each case being contained in a total amount of about 0.01 to 10 percent by weight and preferably of 0.1 to 5 percent by weight in the ready-for-use dyeing agent, which is obtained by mixing the components A1 and A2.

Furthermore, the inventive dyeing agent optionally may contain conventional, physiologically safe direct dyes from the group comprising the nitro dyes, azo dyes, quinone dyes and triphenylmethane dyes.

The direct dyes can be used in the component A1 and the component A2 in each case in a total amount of about 0.02 to 20 percent by weight and preferably of 0.2 to 10 percent by weight, the total amount of direct dyes being about 0.01 to 10 percent by weight and preferably 0.1 to 5 percent by weight in the in the ready-for-use dyeing agent obtained by mixing components A1 and A2.

The dyeing agent A and the components A1 and A2 can be prepared in the form, for example, of a solution, particularly of an aqueous or aqueous alcoholic solution. Further suitable forms of preparation are a cream, a gel, an aerosol foam or an emulsion. Their composition represents a mixture of the enamines of formula (I) and/or of the carbonyl compounds with the additives, which are customary for such preparations.

Conventional additives, used in dyeing agents in solutions, creams, emulsions, gels or aerosol foams are, for example, solvents such as water, low molecular weight aliphatic alcohols, such as ethanol, n-propanol and isopropanol or glycols such as glycerin and 1,2-dihydroxypropane, furthermore wetting agents or emulsifiers from the class of anionic, cationic, amphoteric or nonionic surface active substances, such as fatty alcohol sulfates, ethoxylated fatty alcohol sulfates, alkyl sulfonates, alkylbenzene sulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated esters of fatty acids, furthermore thickneners such as higher molecular weight fatty alcohols, starch or cellulose derivatives, perfumes, hair pre-treatment agents, conditioners, hair swelling agents, preservatives, furthermore petrolatum, paraffin oil and fatty acids, as well as cosmetics, such as cationic resins, lanolin derivatives, cholesterol, pantothenic acid and betaine. The components mentioned are used in amounts, customary for such purposes; for example, the wetting agents and emulsifiers are used in concentrations of 0.5 to 30% by weight (based on the dye composition), the thickener is used in an amount of about 0.1 to 25% by weight (based on the dye composition) and the cosmetics are used in a concentration of about 0.1 to 5.0% by weight (based on the dye composition).

The pH of the ready-for-use dyeing agent A usually is 3 to 11 and preferably 6 to 11, the pH of the ready-for-use dyeing agent being adjusted during the mixing of the enamine-containing component A1, which preferably is alkaline, with the carbonyl-containing component A2, which preferably is acidic, to a value, which is affected by the amount of alkali in the component A1 and the amount of acid in the component A2, as well as by the ratio, in which these two components are mixed.

For adjusting the pH to the value desired for the dyeing, alkalizing agents, such as alkanolamines, alkylamines, alkali hydroxides or ammonium hydroxide and alkali carbonates or ammonium carbonate or acids such as lactic acid, acetic acid, tartaric acid, phosphoric acid, hydrochloric acid, citric acid, ascorbic acid and boric acid can be used.

The ready-for-use dyeing agent A is prepared immediately before use by mixing the enamine-containing component A1 with the component A2, which contains the carbonyl compound, and is then applied to the fibers. Depending on the depth of shade desired, this mixture is allowed to act for 5 to 60 minutes and preferably for 15 to 30 minutes at a temperature of 20 to 50 degrees centigrade and especially of 30 to 40 degrees centigrade. Subsequently, the fiber is rinsed with water and optionally washed with a shampoo.

The inventive dyeing agent A makes possible a gentle, uniform and permanent dyeing of the fibers, especially of keratin fibers, such as hair. Surprisingly, these dyeing can be decolorized completely once again rapidly and gently at any time by reducing agents.

A further object of the present invention therefore is a multi-component kit for dyeing and later decolorizing fibers, such as wool, silk, cotton or hair and especially human hair, wherein the kit contains the inventive dyeing agent A and a decolorizing component B, the latter, as the decolorizing agent, containing at least one sulfite, such as ammonium sulfite, alkali sulfite or alkaline earth sulfite, especially sodium sulfite or ammonium sulfite.

The total amount of sulfites in component B is about 0.1 to 10% by weight and preferably 2 to 5% by weight.

The agent for decolorizing the fibers, dyed with the dyeing agent A (referred to subsequently as "decolorizing agent") may be present as an aqueous or aqueous alcoholic solution, as a gel, a cream, an emulsion or a foam and can be produced in the form of a one-component preparation as well as in the form of a multi-component preparation. The decolorizing agent can be produced as a powder or, for protection against dust formation, also as a tablet—including an effervescent tablet—or as a granulate. From this, with cold or warm water, optionally with the addition of one or more auxiliary materials named in the following, the decolorizing agent is produced before use. It is, however, also possible for these auxiliary materials, provided that they are solids, to be contained already in the decolorizing powder or the decolorizing granulate or the effervescent tablet. Dust formation can be reduced additionally by wetting the powders with oils or waxes.

The decolorizing agent may contain additional auxiliary materials, such as solvents such as water, low molecular weight aliphatic alcohols, such as ethanol, n-propanol and isopropanol, glycol ethers or glycols such as glycerin and, in particular, 1,2-dihydroxypropane, furthermore wetting agents or emulsifiers from the classes of anionic, cationic, amphoteric or nonionic surface active substances, such as fatty alcohol sulfates, ethoxylated fatty alcohol sulfates, alkyl sulfonates, alkylbenzene sulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated esters of fatty acids, furthermore thickneners such as higher molecular weight fatty alcohols, starch or cellulose derivatives, perfumes, hair pre-treatment agents, conditioners, hair swelling agents, preservatives, petrolatum, paraffin oil and fatty acids, as well as cosmetics, such as cationic resins, lanolin derivatives, cholesterol, pantothenic acid and betaine.

The pH of the decolorizing agent is about 3 to 8 and especially 4 to 7. If necessary, the desired pH can be achieved by the addition of suitable acids, such as α-hydroxy carboxylic acids, such as lactic acid, tartaric acid, citric acid or malic acid, phosphoric acid, acetic acid, glycolic acid, salicylic acid, glutathione or gluconic lactone, or by the addition of alkalizing agents such as alkanolamines, alkylamines, alkali hydroxides, ammonium hydroxide, alkali carbonates, ammonium carbonates or alkali phosphates.

The period of action of the decolorizing agent depends on the dyeing that is to be decolorized and on the temperature (about 20 to 50 degrees centigrade) and is 5 to 60 minutes and, in particular, 15 to 60 minutes. The decolorizing process can be accelerated by supplying heat. At the end of the period of action of the decolorizing agent, the hair is rinsed with water and optionally washed with a shampoo.

Although component B is particularly suitable for decolorizing hair, especially human hair, dyed with dyeing agent A, it can also be used to decolorize either natural or synthetic fibers, such as cotton, wool, silk, viscose, nylon and cellulose acetate, which have been dyed with dyeing agent A.

The object of the invention is described in greater detail by the following examples, without being limited to these.

Examples
Examples 1.1 to 1.6: Hair Dyeing Agents

Enamine-Containing Component A1

| | |
|---|---|
| Enamine of formula (I) | Quantitative Data |
| (stabilized with α-tocopherol (vitamin E)) | as in Table 1 |
| cetyl stearyl alcohol | 12.00 g |
| ethoxylated stearyl alcohol with 20 moles | 1.40 g |
| of ethylene oxide in the molecule (Steareth-20) | |
| isopropanol | 20.0 g |
| water, fully desalinated | to 100.0 g |

Aldehyde-Containing Component A2

| | |
|---|---|
| aldehyde compound | Quantitative Date as in Table 1 |
| direct dye | Quantitative Date as in Table 1 |
| cetyl stearyl alcohol | 3.06 g |
| sodium lauryl sulfate | 0.34 g |
| lanolin alcohol | 0.50 g |
| water, fully desalinated | to 100.0 g |

Component A1 (5 g) is mixed with 5 g of component A2. The ready-for-use hair-dyeing agent obtained is applied on bleached hair and distributed uniformly with a brush. After the agent has been allowed to act for a period of 30 minutes at a temperature of 40° C., the hair is washed with a shampoo, then rinsed with lukewarm water and dried.

TABLE 1

Dyeing Results

| No. | a) Enamine-Containing Component A1<br>b) Aldehyde-Containing Component A2 | Shade After Dyeing | | Measured Color Values | | |
|---|---|---|---|---|---|---|
| | | | | L | a | b |
| 1.1 | in a) 1,3,3-trimethyl-2-methylene-indolin, 2.0 g | intensive red | untreated hair | +83.30 | −0.48 | +10.40 |
| | in (b) 4-hydroxy-3-methoxy-benzaldehyde, 1.76 g | | after the dyeing | +25.32 | +58.19 | +12.67 |
| 1.2 | in a) 1,3,3-trimethyl-2-methylene-indolin, 2.0 g | intensive orange | untreated hair | +83.30 | −0.48 | +10.40 |
| | in (b) 4-hydroxybenzaldehyde, 1.43 g | | after the dyeing | +44.34 | +73.22 | +42.70 |
| 1.3 | in a) 1,3,3-trimethyl-2-methylene-indolin, 2.0 g | intensive yellow | untreated hair | +83.3 | −0.48 | +10.40 |
| | in b) 3-hydroxy-4-methoxybenzaldehyde, 1.76 g | | after the dyeing | +58.96 | +33.01 | +66.62 |
| 1.4 | in a) 1,3,3-trimethyl-2-methylene-indolin, 2.0 g | intensive pink | untreated hair | +83.30 | −0.48 | +10.40 |
| | in b) 4-dimethylaminobenzaldehyde 1.72 g | | after the dyeing | +45.75 | +77.26 | +0.54 |
| 1.5 | in a) 1,3,3-trimethyl-2-methylene-indolin, 2.0 g | intensive wine-red | untreated hair | +83.30 | −0.48 | +10.40 |
| | in b) 3,4-dihydroxybenzaldehyde 1.59 g | | after the dyeing | +21.81 | +37.19 | +5.12 |
| 1.6 | in a) 1,3,3-trimethyl-2-methylene-indolin, 2.0 g | intensive red brown | untreated hair | +83.30 | −6.48 | +10.40 |
| | in b) 3,4-dihydroxybenzaldehyde 0.80 g<br>3-hydroxy-4-methoxybenzaldehyde 0.88 g<br>1-(2-hydroxyethyl)amino-2-nitro-4-(di(-2-hydroxyethyl)aminobenzene<br>(HC Blue No. 2) 2.00 g | | after the dyeing | +19.86 | +16.36 | 3.51 |

Examples 1.7 to 1.21: Hair Dyeing Agents

Component A1 Containing Enamine of Formula (1)

| | |
|---|---|
| enamine of Formula (I) | Quantitative Data as in Table 1 |
| 6-O-palmitoyl-L-ascorbic acid | 0.30 g |
| cetyl stearyl alcohol | 12.00 g |
| lauryl ether sulfate, 28% | 10.00 g |
| ethanol | 23.00 g |
| water, fully desalinated | to 100.00 g |

The cetyl stearyl alcohol is melted at 80° C. The lauryl ether sulfate is heated with 95% of the water to 80° C., added to the molten cetyl stearyl alcohol and stirred until a cream results. At room temperature, compound (I) is mixed with the remaining water, the alcohol and the 6-O-palmitoyl-L-ascorbic acid and then added. The pH of the cream is adjusted with 10% aqueous NaOH to a value of 12.0.

Aldehyde-Containing Component A2

| | |
|---|---|
| aldehyde compound | Quantitative Data as in Table 1 |
| direct dye | Quantitative Data as in Table 1 |
| cetyl stearyl alcohol | 12.00 g |
| lauryl ether sulfate, 28% | 10.00 g |
| ethanol | 23.00 g |
| water, fully desalinated | to 100.00 g |

The cetyl stearyl alcohol is melted at 80° C. The lauryl ether sulfate is heated with 95% of the water to 80° C., added to the molten cetyl stearyl alcohol and stirred until a cream results. At room temperature, the aldehyde compound, as well as optionally the direct dyes, mixed with the remaining water and the alcohol, are added. The pH of the cream is adjusted with 10% aqueous lactic acid to a value of 4.0.

Component A1 (5 g) is mixed with 5 g of component A2. The ready-for-use hair-dyeing agent obtained is applied on bleached hair and distributed uniformly with a brush. After the agent has been allowed to act for a period of 30 minutes at a temperature of 40° C., the hair is washed with a shampoo, then rinsed with lukewarm water and dried.

The dyeings obtained are summarized in the following Table 2.

TABLE 2

Dyeing Results

| No. | a) Enamine-Containing Component A1<br>b) Aldehyde-Containing Component A2 | Shade After Dyeing | | Measured Color Values | | |
|---|---|---|---|---|---|---|
| | | | | L | a | b |
| 1.7 | in a) 1,1,2,3-trimethyl-1H-benz(e)-indolinium chloride, 2.99 g<br>in (b) 4-hydroxy-3-methoxybenzaldehyde, 1.76 g | pink-red | untreated hair<br>after the dyeing | +83.30<br>+47.43 | −0.48<br>+50.09 | +10.40<br>+3.75 |
| 1.8 | in a) 1,1,2,3-tetramethyl-1H-benz(e)-indolinium bromide, 3.51 g<br>in b) 4-hydroxybenzaldehyde, 1.43 g | orange | untreated hair<br>after the dyeing | +83.30<br>+60.27 | −0.48<br>+53.71 | +10.40<br>+43.96 |
| 1.9 | in a) 1,1,2,3-tetramethyl-1H-benz(e)-indolinium chloride, 2.99 g<br>in b) 3-hydroxy-4-methoxybenzaldehyde 1.76 g | yellow | untreated hair<br>after the dyeing | +83.30<br>+68.20 | −0.48<br>+22.52 | +10.40<br>+57.04 |
| 1.10 | in a) 1,1,2,3-tetramethyl-1H-benz(e)-indolinium methyl sulfate, 3.86 g<br>in b) 4-dimethylaminobenzaldehyde 1.72 g | pink | untreated hair<br>after the dyeing | +83.30<br>+52.30 | −0.48<br>+47.22 | +10.40<br>−7.93 |
| 1.11 | in a) 1,1,2,3-tetramethyl-1H-benz(e)-indolinium bromide, 3.51 g<br>in b) 3,4-dihydroxybenzaldehyde 1.59 g | wine-red | untreated hair<br>after the dyeing | +83.30<br>+32.40 | −0.48<br>+37.51 | +10.40<br>+1.86 |
| 1.12 | in a) 1,1,2,3-tetramethyl-1H-benz(e)-indolinium iodide, 4.05 g<br>in b) 3,5-dimethoxy-4-hydroxy benzaldehyde, 2.10 g | blue-violet | untreated hair<br>after the dyeing | +83.30<br>+36.10 | −0.48<br>+32.89 | +10.40<br>−17.69 |
| 1.13 | in a) 1,1,2,3-tetramethyl-1H-benz(e)-indolinium chloride 2.99 g<br>in b) 3,4,5-trihydroxybenzaldehyde monohydrate, 1.98 g | petrol | untreated hair<br>after the dyeing | +83.30<br>+21.51 | −0.48<br>+11.82 | +10.40<br>−6.08 |
| 1.14 | in a) 1,1,2,3-tetramethyl-1H-benz(e)-indolinium chloride, 3.00 g<br>in b) 3,4-dihydroxybenzaldehyde, 0.80 g<br>3-hydroxy-4-methoxybenzaldehyde, 0.88 g<br>1-(2-hydroxyethyl)amino-2-nitro-4-(di(2-hydroxyethyl)amino)benzene<br>(HC Blue No. 2). 2.00 g | violet | untreated hair<br>after the dyeing | +83.30<br>+21.43 | −0.48<br>+11.30 | +10.40<br>−6.36 |

TABLE 2-continued

Dyeing Results

| No. | a) Enamine-Containing Component A1<br>b) Aldehyde-Containing Component A2 | Shade After Dyeing | | Measured Color Values | | |
|---|---|---|---|---|---|---|
| | | | | L | a | b |
| 1.15 | (a) 1,2,3,3-tetramethyl-3H-indolinium chloride 2.42 g | intensive red | untreated hair | +83.30 | −0.48 | +10.40 |
| | (b) 4-hydroxy-3-methoxy benzaldehyde 1.76 g | | after the dyeing | +25.32 | +58.19 | +12.67 |
| 1.16 | a) 1,2,3,3-tetramethyl-3H-indolinium chloride 2.42 g | intensive orange | untreated hair | +83.30 | −0.48 | +10.40 |
| | b) 4-hydroxybenzaldehyde, 1.43 g | | after the dyeing | +44.34 | +73.22 | +42.70 |
| 1.17 | a) 1,2,3,3-tetramethyl-3H-indolinium chloride, 2.42 g | intensive yellow | untreated hair | +83.30 | −0.48 | +10.40 |
| | b) 3-hydroxy-4-methoxybenzaldehyde 1.76 g | | after the dyeing | +58.96 | +33.01 | +66.62 |
| 1.18 | a) 1,2,3,3-tetramethyl-3H-indolinium chloride 2.42 g | intensive pink | untreated hair | +83.30 | −0.48 | +10.40 |
| | b) 4-dimethylaminobenzaldehyde 1.72 g | | after the dyeing | +45.75 | +77.26 | +0.54 |
| 1.19 | a) 1,2,3,3-tetramethyl-3H-indolinium chloride 2.42 g | intensive wine-red | untreated hair | +83.30 | −0.48 | +10.40 |
| | b) 3,4-dihydroxybenzaldehyde 1.59 g | | after the dyeing | +21.81 | +37.19 | +5.12 |
| 1.20 | a) 1,2,3,3-tetramethyl-3H-indolinium chloride 2.42 g | intensive violet | untreated hair | +83.30 | −0.48 | +10.40 |
| | b) 3,5-dimethoxy-4-hydroxybenzaldehyde 2.10 g | | after the dyeing | +24.02 | +49.64 | −8.16 |
| 1.21 | a) 1,2,3,3-tetramethyl-3H-indolinium bromide, 2.93 g | intensive red-brown | untreated hair | +83.30 | −0.48 | +10.40 |
| | b) 3,4-dihydroxybenzaldehyde 0.80 g<br>3-hydroxy-4-methoxybenzaldehyde 0.88 g<br>1-(2-hydroxyethyl)amino-2-nitro-4-(di(2-hydroxyethyl)amino)benzene (HC Blue No. 2), 2.00 g | | after the dyeing | +19.86 | +16.36 | +3.51 |

Examples 2.1 to 2.20: Hair Dyeing Agents
Component A1 Containing Enamine

| | |
|---|---|
| enamine of Formula (I) | Quantitative Data as in Table 1 |
| 6-O-palmitoyl-L-ascorbic acid | 0.30 g |
| cetyl stearyl alcohol | 12.00 g |
| lauryl ether sulfate, 28% aqueous solution | 10.00 g |
| ethanol | 23.00 g |
| water, fully desalinated | to 100.00 g |

The cetyl stearyl alcohol is melted at 80° C. The lauryl ether sulfate is heated with 95% of the water to 80° C., added to the molten cetyl stearyl alcohol and stirred until a cream results. At room temperature, compound (I) is mixed with the ethanol/the remaining water and the 6-O-palmitoyl-L-ascorbic acid, and then added. The pH of the cream is adjusted with 10% NaOH solution to a value of 11.0.

Aldehyde-Containing Component A2

| | |
|---|---|
| aldehyde compound | Quantitative Data as in Table 1 |
| cetyl stearyl alcohol | 12.00 g |
| lauryl ether sulfate, 28% aqueous solution | 10.00 g |
| 6-O-palmitoyl-L-ascorbic acid | 0.30 g |
| ethanol | 23.0 g |
| water, fully desalinated | to 100.00 g |

The cetyl stearyl alcohol is melted at 80° C. The lauryl ether sulfate is heated with 95% of the water to 80° C., added to the molten cetyl stearyl alcohol and stirred until a cream results. At room temperature, the aldehyde, mixed with the ethanol and the remaining water as well as the 6-O-palmitoyl-L-ascorbic acid, is added. The pH of the cream is adjusted with 10% aqueous lactic acid to a value of 4.0.

Component A1 and component A2 are mixed in a ratio of 1:1. The ready-for-use hair-dyeing agent, so obtained, is applied on the hair and distributed uniformly with a brush. After the agent has been allowed to act for a period of 30 minutes at a temperature of 40° C., the hair is washed with a shampoo, then rinsed with lukewarm water and dried.

The hair can be decolorized once again completely at 40° C. at any time (for example, after several days or weeks) within a period of 20 minutes with a 5% sodium sulfite solution with a pH of 5 (component B).

The dyeing and decolorizing results obtained are summarized in the following Table.

TABLE 3

| No. | Enamine (1) Contained in A1 Aldehyde contained in A2 | Shade After Dyeing | | Measured Color Values L | a | b | Degree of Decolorization (%) |
|---|---|---|---|---|---|---|---|
| 2.1 | in (A1) 1,2,3,3-tetramethyl-3H-indolinium chloride, 2.42 g in (A2) 4-hydroxy-3-methoxybenzaldehyde, 1.76 g | intensive red | untreated hair after the dyeing after the decolorizing | +83.30 +34.04 +84.19 | −0.48 +68.92 +9.28 | +10.40 +19.11 +18.85 | 86 |
| 2.2 | in (A1) 1,2,3,3-tetramethyl-3H-indolinium chloride, 2.42 g in (A2) 4-hydroxy-benzaldehyde, 1.43 g | intensive orange | untreated hair after the dyeing after the decolorizing | +83.30 +52.07 +82.72 | −0.48 +69.44 11.60 | +10.40 +56.39 +17.04 | 86 |
| 2.3 | in (A1) 1,2,3,3-tetramethyl-3H-indolinium chloride, 2.42 g in (A2) 3-hydroxy-4-methoxy-benzaldehyde, 1.76 g | intensive yellow | untreated hair after the dyeing after the decolorizing | +83.30 +67.01 +84.10 | −0.48 +26.58 +10.52 | +10.40 +78.16 +17.29 | 84 |
| 2.4 | in (A1) 1,2,3,3-tetramethyl-3H-indolinium chloride, 2.42 g in (A2) 3-hydroxy-4-methoxy-benzaldehyde, 1.76 g | intensive violet | untreated hair after the dyeing after the decolorizing | +83.30 +26.06 +80.48 | −0.48 +52.34 +7.83 | +10.40 −6.83 +15.56 | 88 |
| 2.5 | in (A1) 2-methylene-1,3,3-trimethylindolin, 2.00 g in (A2) 3,4-dihydroxy-benzaldehyde, 1.59 g | intensive wine-red | untreated hair after the dyeing after the decolorizing | +83.30 +24.17 +80.6 | −0.48 +41.98 +9.09 | +10.40 +8.34 +19.41 | 82 |
| 2.6 | in (A1) 1,2,3,3-tetramethyl-1H-benz(e)indolinium iodide, 4.05 g in (A2) 3,5-dimethoxy-4-hydroxybenzaldehyde, 1.59 g | black | untreated hair after the dyeing after the decolorizing | +83.30 +23.05 30.81 | −0.48 +7.19 +8.26 | +10.40 +0.35 +12.45 | 85 |
| 2.7 | in (A1) 1,1,2,3-tetramethyl-1H-benz(e)indolinium chloride 2.99 g in (A2) 4-hydroxy-3-methoxy-benzaldehyde, 1.76 g | red after the decolorizing white | untreated hair after the dyeing | +83.30 +47.43 | −0.48 +50.09 | +10.40 +3.75 | |
| 2.8 | in (A1) 1,1,2,3-tetramethyl-1H-benz(e)indolinium chloride 2.99 g in (A2) 4-hydroxybenzaldehyde 1.43 g | orange after the decolorizing white | untreated hair after the dyeing | +83.30 +60.27 | −0.48 +53.71 | +10.40 +43.96 | |
| 2.9 | in (A1) 1,1,2,3-tetramethyl-1H-benz(e)indolinium iodide, 4.05 g in (A2) 3-hydroxy-4-methoxy-benzaldehyde 1.76 g | yellow after the decolorizing white | untreated hair after the dyeing | +83.30 +68.20 | −0.48 +22.52 | +10.40 +57.04 | |
| 2.10 | in (A1) 1,1,2,3-tetramethyl-1H-benz(e)indolinium bromide, 3.51 g in (A2) 4-dimethylamino-benzaldehyde, 1.72 g | pink after the decolorizing white | untreated hair after the dyeing | +83.30 +52.30 | −0.48 +47.22 | +10.40 −7.93 | |
| 2.11 | in (A1) 1,1,2,3-tetramethyl-1H-benz(e)indolinium chloride, 2.99 g in (A2) 3,4-dihydroxy-benzaldehyde, 1.59 g | wine-red after the decolorizing white | untreated hair after the dyeing | +83.30 +32.40 | −0.48 +37.51 | +10.40 +1.86 | |
| 2.12 | in (A1) 1,1,2,3-tetramethyl-1H-benz(e)indolinium chloride, 2.99 g in (A2) 3,5-dimethoxy-4-hydroxybenzaldehyde, 2.10 g | blue-violet after the decolorizing white | untreated hair after the dyeing | +83.30 +36.10 | −0.48 +32.89 | +10.40 −17.69 | |
| 2.13 | in (A1) 1,2,3,3-tetramethyl-3H-indolinium chloride, 2.42 g in (A2) 4-methylimidazol-5-carboxaldehyde, 1.27 g | intensive yellow after the decolorizing white | untreated hair after the dyeing | +83.30 +81.27 | −0.48 −4.04 | +10.40 +94.57 | |
| 2.14 | in (A1) 1,2,3,3-tetramethyl-3H-indolinium chloride, 2.42 g in (A2) 4-hydroxy-2-methoxybenzaldehyde, 1.75 g | intensive yellow after the decolorizing white | untreated hair after the dyeing | +83.30 +47.00 | −0.48 +71.71 | +10.40 +47.92 | |
| 2.15 | in (A1) 1,2,3,3-tetramethyl-3H-indolinium chloride, 2.42 g in (A2) 3,5-dimethyl-4-hydroxybenzaldehyde, 1.73 g | intensive red after the decolorizing white | untreated hair after the dyeing | +83.30 +39.51 | −0.48 +72.92 | +10.40 +24.40 | |
| 2.16 | in (A1) 1,2,3,3-tetramethyl-3H-indolinium chloride, 2.42 g in (A2) 4-dimethylamino-2-methoxybenzaldehyde, 2.10 g | intensive pink after the decolorizing slightly pink | untreated hair after the dyeing | +83.30 +37.36 | −0.48 +76.29 | +10.40 +6.25 | |

TABLE 3-continued

| No. | Enamine (1) Contained in A1 Aldehyde contained in A2 | Shade After Dyeing | | Measured Color Values L | a | b | Degree of Decolorization (%) |
|---|---|---|---|---|---|---|---|
| 2.17 | in (A1) 1,2,3,3-tetramethyl-3H-indolinium chloride, 2.42 g in (A2) 3,4,5-trihydroxy-benzaldehyde, 2.0 g | intensive red-violet after the decolorizing | untreated hair after the dyeing white | +83.30 +19.53 | −0.48 +21.90 | +10.40 −2.69 | |
| 2.18 | in (A1) 1,2,3,3-tetramethyl-1H-benz(e)-indolinium chloride, 2.99 g in (A2) 3,4,5-trihydroxy-benzaldehyde, 2.0 g | blue after the decolorizing | untreated hair after the dyeing white | +83.30 +21.51 | −0.48 +11.82 | +10.40 −6.08 | |
| 2.19 | in (A1) 5-chloro-2-methylene-1,3,3-trimethylindolin, 3.36 g in (A2) 3,4-dihydroxy-benzaldehyde, 1.59 g | wine-red after the decolorizing | untreated hair after the dyeing white | +83.30 +26.67 | −0.48 +45.74 | +10.40 −4.84 | |
| 2.20 | in (A1) 5-chloro-2-methylene-1,3,3-trimethylindolin, 3.36 g in (A2) 4-hydroxy-benzaldehyde, 1.43 g | orange after the decolorizing | untreated hair after the dyeing white | +83.30 +54.25 | −0.48 +67.96 | +10.40 +39.02 | |

Examples 3.1 to 3.2: Hair Dyeing Agents

Enamine-Containing Component A1

| | |
|---|---|
| 1,3,3-trimethyl-2-methylene-indolin | 2.0 g |
| cetyl stearyl alcohol | 12.0 g |
| ethoxylated stearyl alcohol with 20 moles of ethylene oxide in the molecule (Steareth 20) | 1.40 g |
| isopropanol | 20.0 g |
| water, fully desalinated | to 100.0 g |

Aldehyde-Containing Component A2 (3.1)

| | |
|---|---|
| 4-hydroxy-3-methoxybenzaldehyde | 1.76 g |
| cetyl stearyl alcohol | 12.0 g |
| ethoxylated stearyl alcohol with 20 moles of ethylene oxide in the molecule(Steareth 20) | 1.40 g |
| isopropanol | 20.0 g |
| water, fully desalinated | to 100.0 g |

Aldehyde-Containing Component A2 (3.1)

| | |
|---|---|
| 4-hydroxybenzaldehyde | 1.41 g |
| cetyl stearyl alcohol | 12.0 g |
| ethoxylated stearyl alcohol with 20 moles of ethylene oxide in the molecule(Steareth 20) | 1.40 g |
| isopropanol | 20.0 g |
| water, fully desalinated | to 100.0 g |

Component A1 (5 g) is mixed with 5 g of component (A2 3.1 or A2 3.2), which contains the aldehyde. The ready-for-use hair-dyeing agent obtained is applied on bleached light-brown hair and distributed uniformly with a brush. After the agent has been allowed to act for a period of 30 minutes at a temperature of 40° C., the hair is rinsed with lukewarm water and then dried.

Examples 3.3 to 3.4: Hair Dyeing Agent
Enamine-Containing Component A1

| | |
|---|---|
| 1,2,3,3-tetramethyl-3H-indolinium chloride | 2.42 g |
| 6-O-palmitoyl-L-ascorbic acid | 0.30 g |
| cetyl stearyl alcohol | 12.0 g |
| lauryl ether sulfate, 28% | 10.0 g |
| ethanol | 23.0 g |
| water, fully desalinated | to 100.0 g |

The cetyl stearyl alcohol is melted at 80° C. The lauryl ether sulfate is heated with 95% of the water to 80° C., added to the molten cetyl stearyl alcohol and stirred until a cream results. At room temperature, the 1,2,3,3-tetramethyl-3H-indolinium chloride is mixed with the remaining water and the alcohol and mixed with the 6-O-palmitoyl-L-ascorbic acid. The pH of the cream is adjusted with 10% aqueous NaOH to a value of 12.0.

Aldehyde-Containing Component A2 (3.3)

| | |
|---|---|
| 4-hydroxy-3-methoxybenzaldehyde | 1.76 g |
| cetyl stearyl alcohol | 12.0 g |
| lauryl ether sulfate, 28% | 10.0 g |
| ethanol | 23.0 g |
| water, fully desalinated | to 100.0 g |

Aldehyde-Containing Component A2 (3.4)

| | |
|---|---|
| 4-hydroxybenzaldehyde | 1.416 g |
| cetyl stearyl alcohol | 12.00 g |
| lauryl ether sulfate, 28% | 10.00 g |
| ethanol | 23.0 g |
| water, fully desalinated | to 100.0 g |

The cetyl stearyl alcohol is melted at 80° C. The lauryl ether sulfate is heated with 95% of the water to 80° C., added to the molten cetyl stearyl alcohol and stirred until a cream results. At room temperature, the aldehyde, mixed with the remaining water and the alcohol, is added. The pH of the cream (A2/3.3) or (A2/3.4) is adjusted with 10% aqueous lactic acid to a value of 4.0.

Component A1 (5 g), containing the 1,2,3,3-tetramethyl-3H-indolinium chloride, is mixed with 5 g of the aldehyde-containing component (A2/3.3) or A2/3.4). The ready-for-use hair-dyeing agent obtained is applied on bleached light-brown hair and distributed uniformly with a brush. After the agent has been allowed to act for a period of 30 minutes at a temperature of 40° C., the hair is rinsed with lukewarm water and then dried.

During the subsequent washing test, the dyed strands are washed in each case 5 times with a shampoo, rinsed with water and dried. After each washing process, the L*a*b values are determined. The results are summarized in Table 4.

TABLE 4

Dyeing Results and Washing Stability

| No. | Enamine (1) Contained in A1 Aldehyde contained in A2 | Shade After Dyeing | | Measured Color Values | | |
|---|---|---|---|---|---|---|
| | | | | L | a | b |
| 3.1 | in A1: 1,3,3-trimethyl-2-methylene-indolin | intensive red | before the dyeing | 60.31 | +11.53 | +31.63 |
| | in A2: 4-hydroxy-3-methoxy-benzaldehyde, 1.76 g | | after dyeing | 27.60 | +49.86 | +7.56 |
| | | | after 1 wash | 28.44 | +49.48 | +6.63 |
| | | | after 2 washes | 28.24 | +49.14 | +5.55 |
| | | | after 3 washes | 28.66 | +49.78 | +5.47 |
| | | | after 4 washes | 28.27 | +49.25 | +6.39 |
| | | | after 5 washes | 28.16 | +49.15 | +6.34 |
| 3.2 | in A1: 1,3,3-trimethyl-2-methyleneindolin, 2.0 g | intensive orange | before the dyeing | 60.31 | +11.53 | +31.63 |
| | in A2: 4-hydroxybenzaldehyde 1.41 g | | After the dyeing | 40.74 | +55.06 | +34.51 |
| | | | after 1 wash | 39.86 | +54.07 | +31.17 |
| | | | after 2 washes | 39.54 | +53.48 | +29.91 |
| | | | after 3 washes | 40.54 | +53.43 | +31.95 |
| | | | after 4 washes | 39.39 | +52.29 | +28.72 |
| | | | after 5 washes | 39.75 | +51.24 | +29.67 |
| 3.3 | in A1: 1,2,3,3-tetramethyl-3H-indolinium chloride, 2.42 g | intensive red | before the dyeing | 60.31 | +11.53 | +31.63 |
| | in A2: 4-hydroxy=3=methoxy-benzaldehyde, 1.76 g | | after the dyeing | 27.60 | +49.86 | +7.56 |
| | | | after 1 wash | 28.44 | +49.48 | +6.63 |
| | | | after 2 washes | 28.24 | +49.14 | +5.55 |
| | | | after 3 washes | 28.66 | +49.78 | +5.47 |
| | | | after 4 washes | 28.27 | +49.25 | +6.39 |
| | | | after 5 washes | 28.16 | 49.15 | +6.34 |
| 3.4 | in A1: 1,2,3,3-tetramethyl-3H-indolinium chloride, 2.42 g | intense orange | before the dyeing | 60.31 | 11.53 | 31.63 |
| | in A2: 4-hydroxybenzaldehyde 1.41 g | | after the dyeing | 40.74 | +55.06 | +34.51 |
| | | | after 1 wash | 39.86 | +54.07 | +31.17 |
| | | | after 2 washes | 39.54 | +53.48 | +29.91 |
| | | | after 3 washes | 40.54 | +53.43 | +31.95 |
| | | | after 4 washes | 39.39 | +52.29 | +28.72 |
| | | | after 5 washes | 39.75 | +51.24 | +29.67 |

The L*a*b color values, given in the present examples, were measured with a Minolta Chromameter II color measuring device.

The L value here stands for the brightness (that is, the lower the L value, the greater is the color intensity), whereas the "a" value is a measure of the red portion (that is, the higher the "a" value, the greater is the red portion). The b value is a measure of the blue portion of the color and the more negative the b value, the greater is the blue portion.

The D value indicates the color difference, which exists between the untreated strands and the dyed or decolorized strands. It is determined from $$D = \sqrt{((L_i - L_0)^2 + (a_i - a_0)^2 + (b_i - b_0)^2)}$$

in which $L_0$, $a_0$ and $b_0$ are the measured color values of untreated hair and $L_i$, $a_i$ and $b_i$ are the values of the treated hair. The decolorization rate in percent was determined as follows:

decolorization % = (1−(D after decolorization/D after dyeing))×100

Unless stated otherwise, the percentages in the present application represent percentages by weight.

What is claimed is:

1. A multi-component kit for dyeing and, later on, decolorizing fibers, said multi-component kit containing a dyeing-agent-containing component (A) and a decolorizing component (B), said decolorizing component containing at least one sulfite and said dyeing-agent-containing component (A) containing a composition for dyeing fibers;

wherein said composition for dyeing fibers comprises component (A1) containing at least one enamine, or physiologically tolerated salt thereof, and a separate (A2) containing at least one carbonyl compound which are mixed immediately before use, and wherein said at least one enamine is of formula (I):

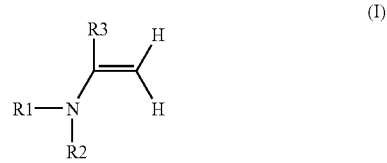

wherein R1 represents an aryl group or an aromatic heterocyclic group, said aryl group having one or more aromatic rings optionally substituted by a C1 to C4 alkyl group, a C1 to C4 hydroxyalkyl group, a hydroxy group, a methoxy group, a dialkylamino group or a halogen group;

wherein R2 represents a linear or branched C1 to C8 alkyl group, a linear or branched C1 to C8 hydroxyalkyl group or a C1 to C8 alkoxyalkyl group with optional oxygen atoms between carbon atoms of the alkyl, hydroxyalkyl and alkoxyalky groups;

wherein R3 represents a linear or branched C1 to C8 alkyl group, a C1 to C8 alkoxyalkyl group, a linear or branched C1 to C8 alkylene group or a C1 to C8 alkoxyalkylene group, —O—, —NH—, —NR$_4$— or —S— with R$_4$ being hydrogen, an alkyl group, an alkoxyalkyl group or a hydroxyalkyl group; or wherein R1 and R3 together with nitrogen and carbon atoms of the basic enamine structure form a cyclic group.

2. A multi-component kit for dyeing and, later on, decolorizing fibers, said multi-component kit comprising
a first component (A1) containing at least one enamine, or a physiologically tolerated salt thereof;
a second component (A2) containing at least one carbonyl compound; and
an additional decolorizing component (B) containing at least one sulfite;
wherein a composition for dyeing the fibers is made by mixing said first component (A1) with said second component (A2); and
wherein said at least one enamine is of formula (I):

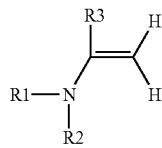

(I)

wherein R1 represents an aryl group or an aromatic heterocyclic group, said aryl group having one or more aromatic rings optionally substituted by a C1 to C4 alkyl group, a C1 to C4 hydroxyalkyl group, a hydroxy group, a methoxy group, a dialkylamino group or a halogen group;

wherein R2 represents a linear or branched C1 to C8 alkyl group, a linear or branched C1 to C8 hydroxyalkyl group or a C1 to C8 alkoxyalkyl group with optional oxygen atoms between carbon atoms of the alkyl, hydroxyalkyl and alkoxyalky groups;

wherein R3 represents a linear or branched C1 to C8 alkyl group, a C1 to C8 alkoxyalkyl group, a linear or branched C1 to C8 alkylene group or a C1 to C8 alkoxyalkylene group, —O—, —NH—, —NR$_4$— or —S— with R$_4$ being hydrogen, an alkyl group, an alkoxyalkyl group or a hydroxyalkyl group; or wherein R1 and R3 together with nitrogen and carbon atoms of the basic enamine structure form a cyclic group.

3. The multi-component kit as defined in claim 2, wherein the at least one sulfite is selected from the group consisting of ammonium sulfites, alkali sulfites and alkaline earth sulfites.

4. The multi-component kit as defined in claim 2, wherein the at least one sulfite is contained in said decolorizing component in a total amount of 0.1 to 10 percent by weight.

5. The multi-component kit as defined in claim 2, wherein R1 is a phenyl group, a pyridyl group or a napthyl group.

6. The multi-component kit as defined in claim 2, wherein the aryl group is a 5-membered or 6-membered aryl group or the aromatic heterocyclic group is a 5-membered or 6-membered aromatic heterocyclic group.

7. The multi-component kit as defined in claim 2, wherein said at least one enamine is selected from the group consisting of 3-ethyl-2-methylenebenzothiazolin; 2-methylene-1,3,3-trimethylindolin; 1,2,3,3-tetramethyl-3H-indolinium chloride; 1,2,3,3-tetramethyl-3H-indolinium bromide; 1,2,3,3-tetramethyl-3H-indolinium iodide; 1,2,3,3-tetramethyl-3H-indolinium sulfate; 1,2,3,3-tetramethyl-3H-indolinium hydrogen sulfate; 1,2,3,3-tetramethyl-3H-indolinium methyl sulfate; 1,2,3,3-tetramethyl-3H-indolinium hexafluorophosphate; 1,2,3,3-tetramethyl-3H-indolinium hexafluaroantimonate; 1,2,3,3-tetramethyl-3H-indolinium tetrafluoroborate; 5-chloro-2-methylene-1,3,3-trimethylindolin; 1-(2-hydroxyethyl)-3,3-dimethyl-2-methylene-indolin; 1,1,2,3-tetramethyl-1H-benz(e)indolinium chloride; 1,1,2,3-tetramethyl-1H-benz(e)indolinium bromide; 1,1,2,3-tetramethyl-1H-benz(e)indolinium iodide; 1,1,2,3-tetramethyl-1H-benz(e)indolinium sulfate; 1,1,2,3-tetramemyl-1H-benz(e)indolinium hexafluoro-phosphate; 1,1,2,3-tetramethyl-1H-benz(e)indolinium methyl sulfate; 1,1,2,3-tetra-methyl-1H-benz(e)indolinium hexafluoroantimonate and 1,1,2,3-tetramethyl-1H-benz(e)indolinium tetrafluoroborate.

8. The multi-component kit as defined in claim 2, wherein said at least one carbonyl compound is selected from the group consisting of 4-hydroxy-3-methoxybenzaldehyde; 3-hydroxy-4-methoxy-benzaldehyde; 3,4-dihydroxy-benzaldehyde; 4-hydroxybenzaldehyde; 3,5-dimethoxy-4-hydroxybenzaldehyde; 4-dimethylaminobenzaldehyde; 4-methyl-5-imidazolcarboxaldehyde; 4-dimethyl-amino-cinnamaldehyde; 4-hydroxy-2-methoxy-benzaldehyde; 3,5-dimethyl-4-hydroxybenzaldehyde; 4-dimethylamino-2-methoxybenzaidehyde; 2-hydroxy-benzaldehyde; 4-hydroxyl-1-naphthaldehyde; 4-methoxy-1-naphthaldehyde; 4-dimethylamino-1-naphthaidehyde; 4'-hydroxy-biphenyl-1-carbaldehyde; 2-hydroxy-3-methoxy-benzaldehyde; 2,4-dihydroxybenzaldehyde; 3,4-dihydroxybenzaldehyde; 2,5-dihydroxybenzaldehyde; 2,3,4-trihydroxybenzaldehyde; 3,4,5-trihydroxy-benzaldehyde; 2,4,6-trihydroxybenzaldehyde; 2,4-dimethoxy-benzaldehyde; 2,3-dimethoxybenzaldehyde; 2,5-dimethoxybenzaldehyde; 3,5-dimethoxy-benzaldehyde; 3,4-dimethoxybenzaldehyde; indole-3-carbaldehyde; benzene-1,4-dicarbaldehyde; 4-ethoxybenzaldehyde; 2-methyl-1,4-naphthoquinone; 4-carboxybenzaldehyde; 4-hydroxy-3-methoxy-cinnamaldehyde; 3,5-dimethoxy-4-hydroxy-cinnamaldehyde; 3-methoxy-4-(1-pyrrolidinyl)-benzaldehyde; 4-diethylamino-3-methoxybenzaldehyde; 1,2-phthaldehyde; pyrrole-2-aldehyde; thiophene-2-aldehyde; thiophene-3-aldehyde; chromone-3-carboxaldehyde; 6-methyl-4-oxo-1(4H)-benzopyran-3-carbaldehyde; N-methylpyrrole-2-aldehyde; 5-methylfurfural; 6-hydroxy-chromene-3-carboxyaldehyde; 6-methylindole-3-carboxaldehyde; 4-dibutyl-aminobenzaldehyde; N-ethylcarbazol-3-aldehyde; 4-diethylamino-2-hydroxybenzaldehyde; 3,4-dimethoxy-5-hydroxybenzaldehyde; 5-(4-(diethylamino)-phenyl-2,4-pentadienal; 2,3-thiophenedcarboxaldehyde; 2,5-thiophene-dicarboxaldehyde; 2-methoxy-1-naphthaldehyde; 3-ethoxy-4-hydroxybenzaldehyde; 2-nitrobenzaldehyde; 3-nitrobenzaldehyde and 4-nitrobenzaldehyde.

9. The multi-component kit as defined in claim 2, wherein said at least one enamine or said salt is at least one of compounds of formula (II) to (IX):

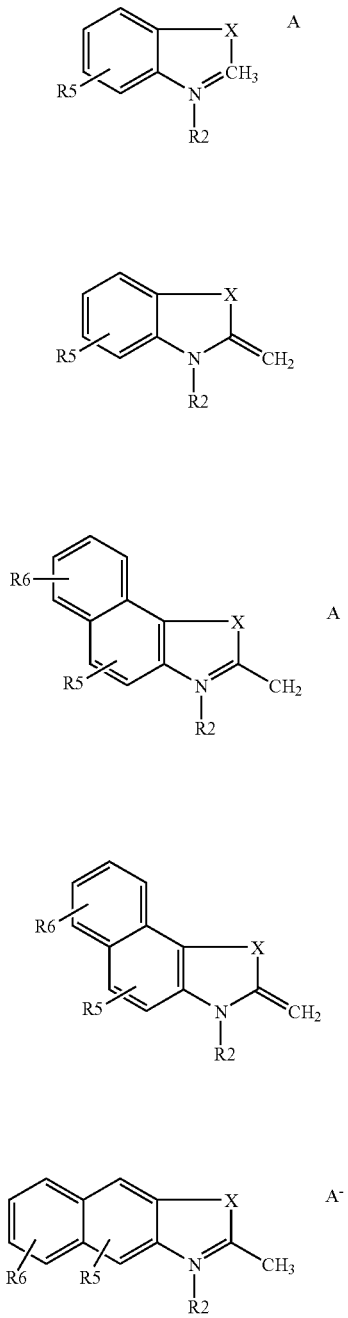

wherein X represents a carbon atom, which is substituted by two C1 to C4 alkyl groups or by a C1 to C4 alkyl group and a hydroxyl group; a sulfur atom; an alkylated or not alkylated nitrogen atom or an oxygen atom;

wherein R2 represents a linear or branched C1 to C8 alkyl group, a linear or branched C1 to C8 hydroxyalkyl group or a C1 to C8 alkoxyalkyl group, with optional oxygen atom substitution between alkyl carbon atoms;

wherein R5 and R6, independently of one another, represent hydrogen, a linear or branched C1 to C4 alkyl group, a linear or branched C1 to C4 hydroxyalkyl group, a hydroxy group, a methoxy group, an amino group, a dialkylamino group or a halogen atom; and wherein $A^-$ represents chloride, bromide, iodide, hydrogen sulfate, monomethyl sulfate, sulfate, hexafluorophosphate, hexafluoroantimonate, tetrafluoroborate or tetraphenyl borate.

10. The multi-component kit as defined in claim 2, wherein said composition for dyeing the fibers contains from 0.01 to 10 percent by weight of said at least one enamine and from 0.01 to 10 percent by weight of the at least one carbonyl compound.

11. The multi-component kit as defined in claim 2, wherein said composition for dyeing the fibers has a pH of 3 to 11.

12. A method of temporarily dyeing and later decolorizing hair, said method comprising the steps of:
   a) applying a dye composition for temporarily dyeing to the hair and allowing the dye composition for temporarily dyeing to act on the hair; and then
   b) treating the hair temporarily dyed in step a) at a later time with a sulfite-containing containing preparation for a period of 5 to 60 minutes at a temperature of 20° C. to 50° C.;
   wherein the dye composition is made by mixing one component (A1) containing at least one enamine, or physiologically tolerated salt thereof, with another component (A2) containing at least one carbonyl compounds, and wherein said at least one enamine is of formula (I):

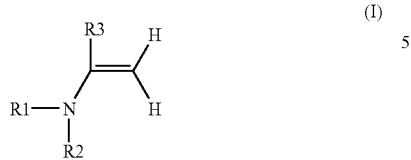

wherein R1 represents an aryl group or an aromatic heterocyclic group, said aryl group having one or more aromatic rings optionally substituted by a C1 to C4 alkyl group, a C1 to C4 hydroxyalkyl group, a hydroxy group, a methoxy group, a dialkylamino group or a halogen group;

wherein R2 represents a linear or branched C1 to C8 alkyl group, a linear or branched C1 to C8 hydroxyalkyl group or a C1 to C8 alkoxyalkyl group with optional oxygen atoms between carbon atoms of the alkyl, hydroxyalkyl and alkoxyalky groups;

wherein R3 represents a linear or branched C1 to C8 alkyl group, a C1 to C8 alkoxyalkyl group, a linear or branched C1 to C8 alkylene group or a C1 to C8 alkoxyalkylene group, —O—, —NH—, —NR$_4$— or —S— with R$_4$ being hydrogen, an alkyl group, an alkoxyalkyl group or a hydroxyalkyl group; or wherein R1 and R3 together with nitrogen and carbon atoms of the basic enamine structure form a cyclic group.

13. The method as defined in claim 12, wherein the dye composition is allowed to act on the hair for a time period of 5 to 60 minutes at a temperature of 20 to 50° C., depending on a predetermined depth of color shade of the dyed hair.

14. The method as defined in claim 12, wherein the sulfite-containing preparation has a pH of 3 to 8, contains from 0.1 to 10% by weight of at least one sulfite and water and said at least one sulfite is selected from the group consisting of ammonium sulfites, alkali sulfites and alkaline earth sulfides.

* * * * *